(12) United States Patent
Stout et al.

(10) Patent No.: US 8,388,583 B2
(45) Date of Patent: Mar. 5, 2013

(54) SYSTEMS AND METHODS FOR PROVIDING A FLUSHABLE CATHETER ASSEMBLY

(75) Inventors: Marty L. Stout, South Weber, UT (US); S. Ray Isaacson, Roy, UT (US); Mark Spinti, Flagstaff, AZ (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 575 days.

(21) Appl. No.: 12/544,625

(22) Filed: Aug. 20, 2009

(65) Prior Publication Data
US 2011/0046570 A1    Feb. 24, 2011

(51) Int. Cl.
*A61M 5/00* (2006.01)
(52) U.S. Cl. .......... 604/244; 604/246; 604/249
(58) Field of Classification Search ............ 604/164.01, 604/164.02, 167.01–167.06, 168.01, 172, 604/200, 246, 244, 249
See application file for complete search history.

(56) References Cited

U.S. PATENT DOCUMENTS

| | | |
|---|---|---|
| 4,387,879 A | 6/1983 | Tauschinski |
| 4,449,693 A | 5/1984 | Gereg |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A * | 8/1990 | Hibbs et al. .......... 604/265 |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |

(Continued)

FOREIGN PATENT DOCUMENTS

| CA | 2133053 A1 | 3/1995 |
|---|---|---|
| DE | 20 2009 009 602 U1 | 1/2010 |

(Continued)

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Theodore Stigell
(74) *Attorney, Agent, or Firm* — Jeanne Lukasavage; Craig Metcalf; Kirton McConkie (57) ABSTRACT

A flushable catheter assembly having features to enable selective activation of fluid flow through the catheter assembly is disclosed herein. A septum is placed within the catheter adapter of the catheter assembly and includes a pathway that is closed prior to being biased open via a septum activator also positioned within the catheter adapter. A plurality of air vent channels is interposed between the septum and the inner surface of the catheter adapter to permit "flashback" of blood during insertion of the catheter into a patient. The septum activator is advanced through the pathway of the septum as a coupler is attached to a proximal opening of the catheter adapter.

12 Claims, 9 Drawing Sheets

U.S. PATENT DOCUMENTS

| | | |
|---|---|---|
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1* | 10/2007 | Adams .................. 604/168.01 |
| 2008/0039796 A1 | 2/2008 | Nakajima |
| 2008/0108944 A1 | 5/2008 | Woehr et al. |
| 2010/0204675 A1 | 8/2010 | Woehr et al. |
| 2010/0222746 A1 | 9/2010 | Burkholz |

FOREIGN PATENT DOCUMENTS

| | | |
|---|---|---|
| EP | 1 679 043 A1 | 7/2006 |
| EP | 1 679 043 A1 | 7/2006 |
| WO | WO 99/34849 | 7/1999 |
| WO | 2008/052790 A2 | 5/2008 |
| WO | 2009/114833 A1 | 9/2009 |
| WO | 2010/093791 A1 | 8/2010 |

* cited by examiner

SYSTEMS AND METHODS FOR PROVIDING A FLUSHABLE CATHETER ASSEMBLY

BACKGROUND OF THE INVENTION

The current invention relates to infusion devices, specifically to peripheral intravenous (IV) catheters. In particular, the invention relates to a flushable peripheral IV catheter assembly having features to enable selective activation of fluid flow through the catheter assembly.

Catheters are commonly used for a variety of infusion therapies. For example, catheters are used for infusing fluids, such as normal saline solution, various medicaments, and total parenteral nutrition, into a patient, withdrawing blood from a patient, or monitoring various parameters of the patient's vascular system.

Catheters and/or needles are typically coupled to a catheter adapter to enable attachment of IV tubing to the catheter. Thus, following placement of the catheter or needle into the vasculature of a patient, the catheter adapter is coupled to a fluid source via a section of IV tubing. In order to verify proper placement of the needle and/or catheter in the blood vessel, the clinician generally confirms that there is "flashback" of blood in a flashback chamber of the catheter assembly.

Once proper placement of the catheter is confirmed, the clinician must then attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the needle or catheter into the vein of the patient. While this method may prevent undesirable exposure to blood, positive pressure within the IV line may also prevent desirable flashback.

Accordingly, there is a need in the art for a catheter assembly that permits desirable flashback without the risk of encountering undesirable exposure to blood. Such a catheter assembly is disclosed herein.

BRIEF SUMMARY OF THE INVENTION

In order to overcome the limitations discussed above, the present invention relates to a flushable peripheral IV catheter assembly having features to enable selective activation of fluid flow through the catheter assembly. The catheter assembly of the present invention generally includes a catheter coupled to a catheter adapter. The catheter generally includes a metallic material, such as titanium, surgical steel or an alloy as is commonly known in the art. In some embodiments, a polymeric catheter may be used in combination with a metallic introducer needle, as is commonly known and used in the art.

In some embodiments of the present invention, a septum is positioned within a lumen of the catheter assembly to prevent or limit flow of a fluid through the catheter adapter. The septum generally includes a flexible or semi-flexible material that is compatible with exposure to blood, medicaments, and other fluids commonly encountered during infusion procedures. In some embodiments, a groove is provided on an inner surface of the catheter adapter, wherein the septum is seated within the groove. As such, the position of the septum within the catheter adapter is maintained.

A closed or partially closed pathway, such as a slit or small hole is further provided in a barrier surface of the septum. The pathway permits fluid to bypass the septum and flow though the catheter adapter. In some embodiments, the pathway is a slit that is closed prior to being opened or activated by a probe or septum activator positioned within the lumen of the catheter adapter. Prior to being opened or activated, the slit prevents passage of fluid through the catheter adapter. Thus, in some embodiments a plurality of air vent channels are interposed between the septum and the groove to permit air flow through the catheter adapter prior to the slit being opened. The air vents prevent buildup of positive pressure within the catheter adapter thereby permitting flashback of blood into the catheter and a forward chamber of the catheter adapter.

The septum activator generally includes a plastic or metallic tubular body having a probing end and a contact end. The probing end is positioned adjacent to the pathway of the septum, and the contact end is positioned adjacent to a proximal opening of the catheter adapter. The probing end of the septum activator is advanced through the pathway of the septum when a probe is inserted into the proximal opening of the catheter adapter. As the probe contacts the contact surface of the septum activator, the septum activator is advanced in a distal direction through the catheter adapter whereupon the probing end of the septum activator opens the pathway in the septum. Once opened, free flow of fluid is enabled through the catheter assembly.

Finally, the presence of the septum activator within the lumen of the catheter adapter may result in aberrant fluid flow leading to undesirable stagnation and coagulation of fluids within the catheter assembly. Thus, in some embodiments of the present invention the septum activator further includes various flow deflectors and/or flow diversion channels to maintain proper fluid flow within the catheter adapter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
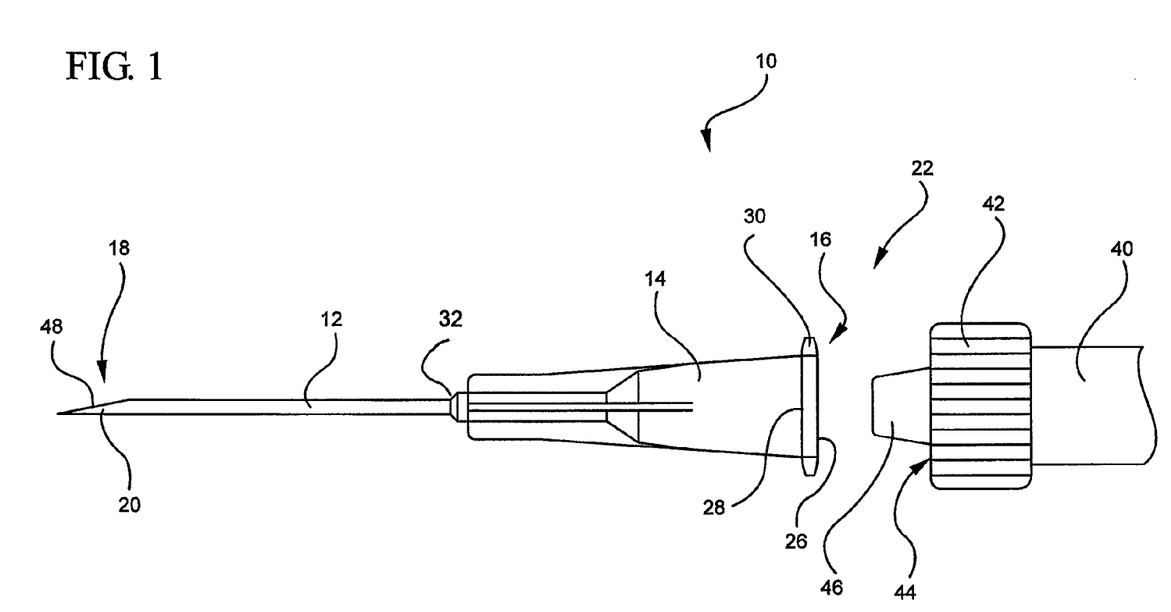
FIG. 1 is a perspective view of an embodiment of a catheter assembly in accordance with the present invention.

Referring now to FIG. 1, a catheter assembly 10 is illustrated. The catheter assembly 10 generally includes a catheter 12 coupled to a distal end 32 of a catheter adapter 14. The catheter 12 and the catheter adapter 14 are integrally coupled such that an internal lumen 16 of the catheter adapter 14 is in fluid communication with a lumen 18 of the catheter 12. The catheter 12 generally comprises a biocompatible material having sufficient rigidity to withstand pressures associated with insertion of the catheter into a patient. In some embodiments, the catheter 12 comprises a metallic material, such as titanium, stainless steel, nickel, molybdenum, surgical steel, and alloys thereof. In other embodiments, the catheter 12 comprises a rigid, polymer material, such as vinyl. A tip portion 20 of the catheter is generally configured to include a beveled cutting surface 48. The beveled cutting surface 48 is utilized to provide an opening in a patient to permit insertion of the catheter 12 into the vascular system of the patient.

One of skill in the art will appreciate that the features of the present invention may be incorporated for use with an over-the-needle catheter assembly. For example, one of skill in the art will appreciate that a flexible or semi-flexible polymer catheter may be used in combination with a rigid introducer needle to enable insertion of the catheter into a patient. One of skill in the art will further appreciate that surgically implanted catheters may also be used in combination with the present invention.

Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing 40 to further facilitate delivery of a fluid to or removal of a fluid from a patient.

In some embodiments, a proximal end 22 of the catheter adapter 14 includes a flange 28. The flange 28 provides a positive surface which may be configured to enable coupling of an intravenous tubing or patient conduit 40 to the catheter assembly 10. In some embodiments, the flange 28 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit 40 in a fluid-tight manner.

In some embodiments, an inner portion of the conduit coupler 42 is extended outwardly to provide a probe surface 46.

Figure 4:
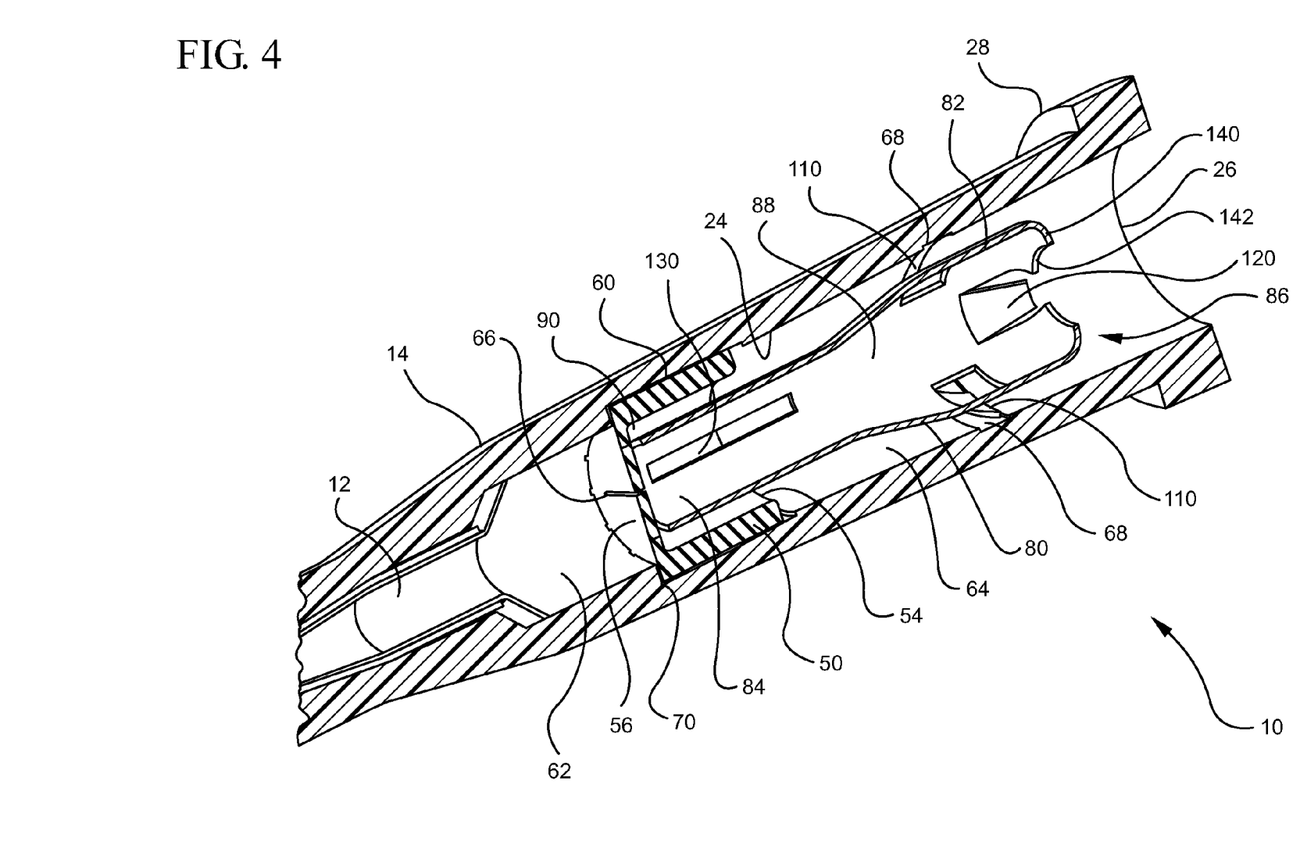
FIG. 4 is a cross-sectioned view of an assembled catheter assembly in accordance with the present invention, prior to activation.

The probe surface 46 is generally configured to compatibly insert within a proximal end 22 of the catheter adapter 14. Following insertion of the probe 46 into the proximal end 22 of the catheter adapter 14, the conduit coupler 42 is rotated to interlock the coupler 42 and the flange 28 (via the sets of threads 30 and 44). During the process of interlocking the coupler 42 and the flange 28, the probe 46 is advanced into the lumen 16 of the catheter adapter 14 to an inserted position (as shown in FIG. 4). The inserted position of the probe surface 46 activates the catheter assembly 10 to enable flow of fluid through the catheter 12 and catheter adapter 14. Once the conduit coupler 42 and the catheter adapter 14 are attached, a fluid may be delivered to a patient via the patient conduit 40 and the inserted catheter 12.

Figure 2A:
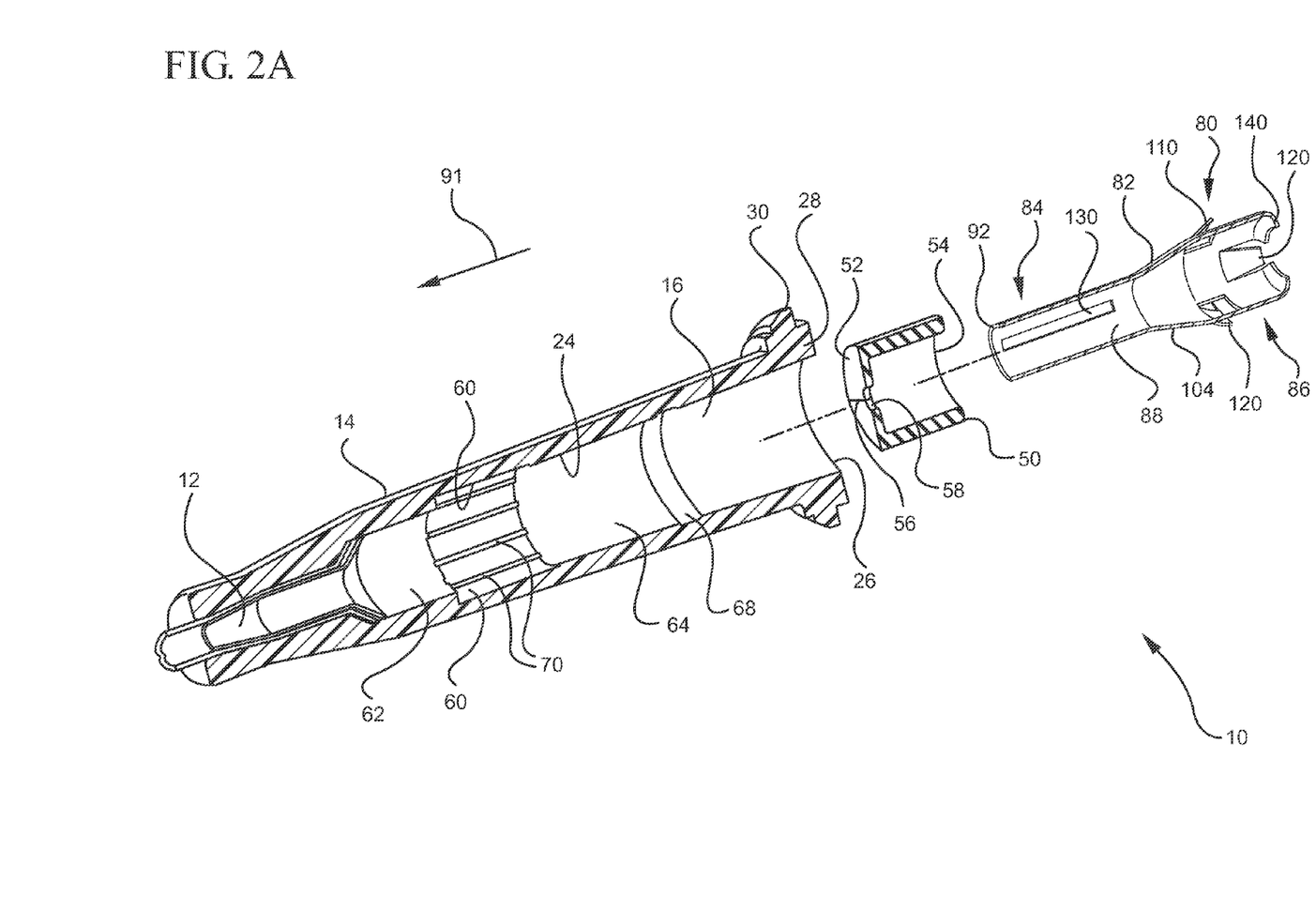
FIG. 2A is an exploded cross-sectioned view of a catheter assembly in accordance with the present invention.

Referring now to FIG. 2A, an exploded, cross-sectional view of a catheter assembly 10 is shown. In some embodiments, the catheter adapter 14 includes various design features and components to control and/or limit flow of fluid through the catheter assembly 10. For example, in some embodiments of the present invention a septum 50 is positioned within the inner lumen 16 of the catheter adapter 14. The septum 50 generally comprises a flexible, or semi-flexible polymer plug having an outer diameter that is configured to compatibly seat within a groove or channel 60 formed on an inner surface 24 of the catheter adapter 14. In some embodiments, the septum 50 is barrel shaped having a barrier surface 52 comprising a distal end of the septum 50 and further having an opening 54 comprising a proximal end of the septum 50. When positioned within the channel 60, the barrier surface 52 of the septum 50 divides the inner lumen 16 of the catheter adapter 14 into a forward fluid chamber 62 and a rearward fluid chamber 64. Thus, the presence of the septum 50 controls or limits passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, the slit 56 is configured to remain in a closed, fluid-tight position until activated or opened by advancing a septum activator 80 through the slit 56 in a distal direction 91. In some embodiments, the barrier surface 52 comprises one slit 56. In other embodiments, the barrier surface 52 is modified to include multiple slits 56 and 66, as shown in FIG. 4.

For some infusion therapy techniques, it may be desirable to permit a controlled flow of fluid through the septum 50 prior to activating the septum 50 with the septum activator 80. Thus, in some embodiments the slit 56 further comprises a leak orifice 58. The leak orifice 58 is positioned in the barrier surface 52 and comprises an opening diameter calculated to permit controlled flow of liquid or air between the forward and rearward chambers 62 and 64. In some embodiments, the barrier surface 52 is modified to include a single leak orifice 58. In other embodiments, the barrier surface 52 is configured to include multiple leak orifices. Still, in other embodiments the bather surface 52 does not include a slit 56, but rather includes at least one leak orifice 58. For these embodiments, the septum 50 generally comprises an elastic material such that when the septum activator 80 is advanced in a distal direction 91, a leading edge 92 of the septum activator 80 contacts the barrier surface 52 and stretches the leak orifice 58 to provide a larger orifice thereby permitting increased flow of air and/or fluid through the catheter adapter 14.

The groove or channel 60 into which the septum is seated comprises a recessed portion of the inner surface 24 of the catheter adapter 14. The outer diameter of the septum 50 is generally configured to compatibly and securely seat within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10.

For some infusion therapy techniques, air flow between the forward and rearward chambers 62 and 64 may be desirable. For example, for those embodiments comprising a septum 50 having a fluid-tight slit 56, passage of air from the forward chamber 62 to the rearward chamber 64 is prohibited prior to opening or activating the septum 50 via the septum activator 80, as previously discussed. Thus, when the catheter 12 of the catheter assembly 10 is inserted into the vascular system of a patient, a positive pressure develops within the forward chamber 62 thereby preventing a desired flashback of the patient's blood into the catheter adapter 14. An observable flashback is generally desirable to confirm accurate placement of the catheter tip 20 within the vein of the patient. Thus, some embodiments of the present invention include features or elements to enable airflow between the forward chamber 62 and the rearward chamber 64, without requiring activation of the septum 50 with the septum activator 80. As such, some embodiments of the present invention provide an observable flashback, as generally desired for infusion procedures.

For example, in some embodiments the barrier surface 52 of the septum 50 is modified to include leak orifice 58, as previously discussed. In other embodiments, a plurality of air vent channels 70 is interposed between the septum 50 and the inner surface 24 of the catheter adapter 14. The air vent channels 70 relieve the positive pressure within the forward chamber 62 by providing an access for air to bypass the septum 50 into the rearward chamber 64. In some embodiments, the air vent channels 70 are constructed by removing portions of the channel 60 surface, resulting in a plurality of generally parallel grooves.

In addition to permitting air flow between the forward and rearward chambers 62 and 64, the vent channels 70 may be configured to permit fluid to flow through the catheter adapter 14 prior to activating or opening the slit 56 with the septum activator 80. In some embodiments, the rate at which air and/or fluid flows between the forward and rearward chambers 62 and 64 is adjusted by manufacturing the catheter adapter 14 to include a greater or lesser number of vent channels 70. In other embodiments, the rate at which air and/or fluid flows between the forward and rearward chambers 62 and 64 is adjusted by manufacturing the catheter adapter 14 to include vent channels 70 having a greater or lesser cross-sectioned area. Thus, in some embodiments the rate at which air and/or fluid flows between the forward and rearward chambers 62 and 64 is increased by manufacturing a catheter adapter 14 having either an increased number of vent channels 70, or vent channels 70 having a greater cross-sectioned area. Conversely, in other embodiments the rate at which air and/or fluid flows between the forward and rearward chambers 62 and 64 is decreased by manufacturing a catheter adapter 14 having either a decreased number of vent channels 70, or vent channels 70 having a lesser cross-sectioned area.

With continued reference to FIG. 2A, the septum activator 80 comprises a probe-like structure that is primarily housed in the rearward chamber 64 of the catheter adapter 14. The septum activator 80 generally comprises a tubular body 82 having a distal end 84 and a proximal end 86. The tubular body 82 comprises a rigid or semi-rigid material, such as a plastic or metallic material. The tubular body 82 further comprises an inner lumen 88 for facilitating flow of a fluid and/or liquid through the septum activator 80.

The distal end 84 of the tubular body 82 is configured to compatibly insert within the opening 54 of the septum 50. The distal end 84 further includes a probing surface 90 which extends through the opening 54 of the septum 50 to a position proximal to the barrier surface 52 of the septum 50, as shown in FIG. 4. The probing surface 90 is advanced through the slit 56 and 66, or through the leak orifice 58 as the septum activator is advanced through the catheter adapter 14 in a distal direction 91. Advancement of the septum activator 80 through the catheter adapter 14 will be discussed in detail below, in connection with FIGS. 4 and 5.

Still, in other embodiments the septum 50 is coated with a hydrophobic coating, or a polymeric swelling coating to repel or prevent fluid from flowing through the vent channels 70. A hydrophobic coating is generally selected to reduce the surface energy of the septum 50 and/or adapter 14 to inhibit blood wicking into the air vents 70. In some embodiments, a surface of the septum 50 or catheter adapter 14 is coated with a polyxylylene polymer material, such as parylene. Parylene is a chemically resistant coating with good barrier properties for inorganic and organic fluids, strong acids, caustic solutions, gases and water vapors. In some embodiments, a parylene coating is applied to the outer surface of the septum 50 via vapor deposition. In other embodiments, a polyxylylene polymer coating is applied to a vent channel 70 via vapor deposition.

In some embodiments, a dehydrated polymer material is applied to a surface of the septum 50 or catheter adapter 14 which comprises the vent channels 70. A dehydrated polymer is generally selected to expand or swell upon contact with fluid. As such, when the dehydrated polymer swells, a flow through the vent channels 70 is blocked or occluded by the swollen polymer. Initially, the dehydrated polymer generally comprises a thin profile prior to exposure to moisture. However, when exposed to moisture the polymer absorbs the moisture which increases the profile of the polymer to block flow through the vent 70. Therefore, by coating the septum 50 and/or catheter adapter 14 with a desired coating, flow of air is permitted between the forward and rearward chambers 62 and 64, yet fluid flow through the vent channels 70 is prevented.

Figure 2B:
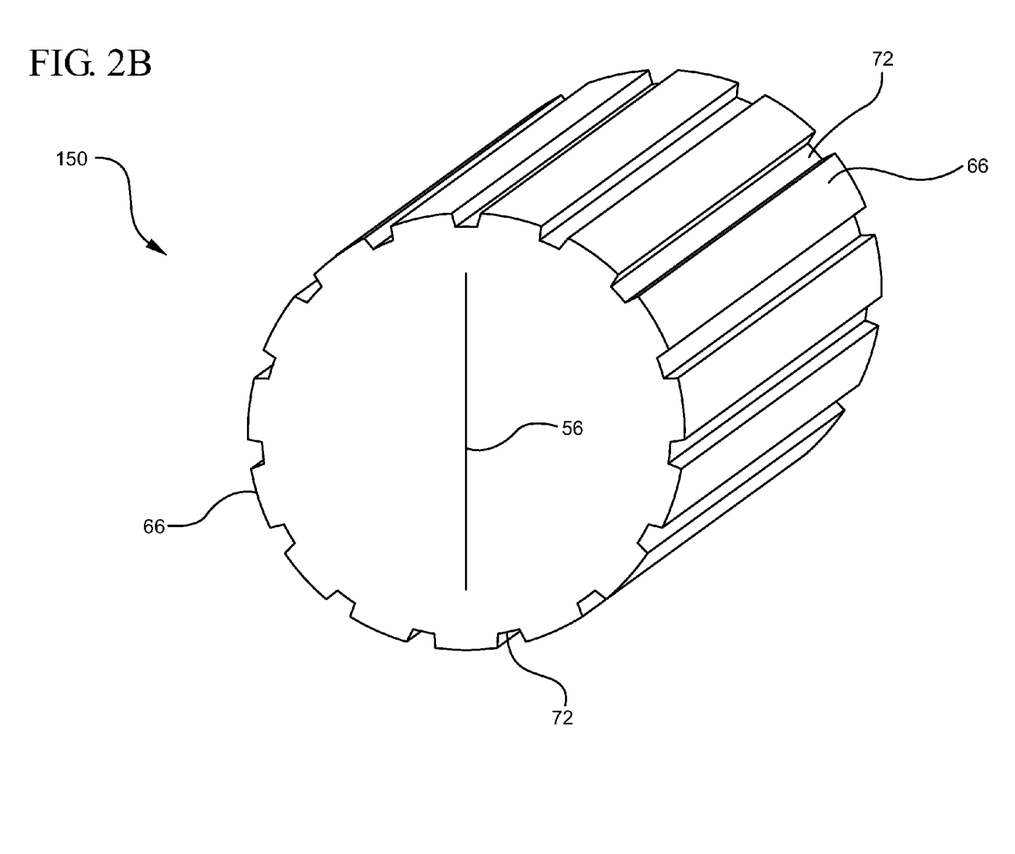
FIG. 2B is a perspective view of an embodiment of a septum in accordance with the present invention.

Referring now to FIG. 2B, an embodiment of a septum 150 is shown. In some embodiments, an outer surface 66 of the septum 150 is modified to include a plurality of recessed grooves 72. The recessed grooves 72 provide pathways between the forward and rearward chambers 62 and 64 through which air and/or fluid may flow. Thus, in some embodiments the channel 60 does not include air vent channels 70, but rather the outer surface 66 of the septum 150 is modified to provide desired flow between the forward and rearward chambers 62 and 64.

Figure 3A:
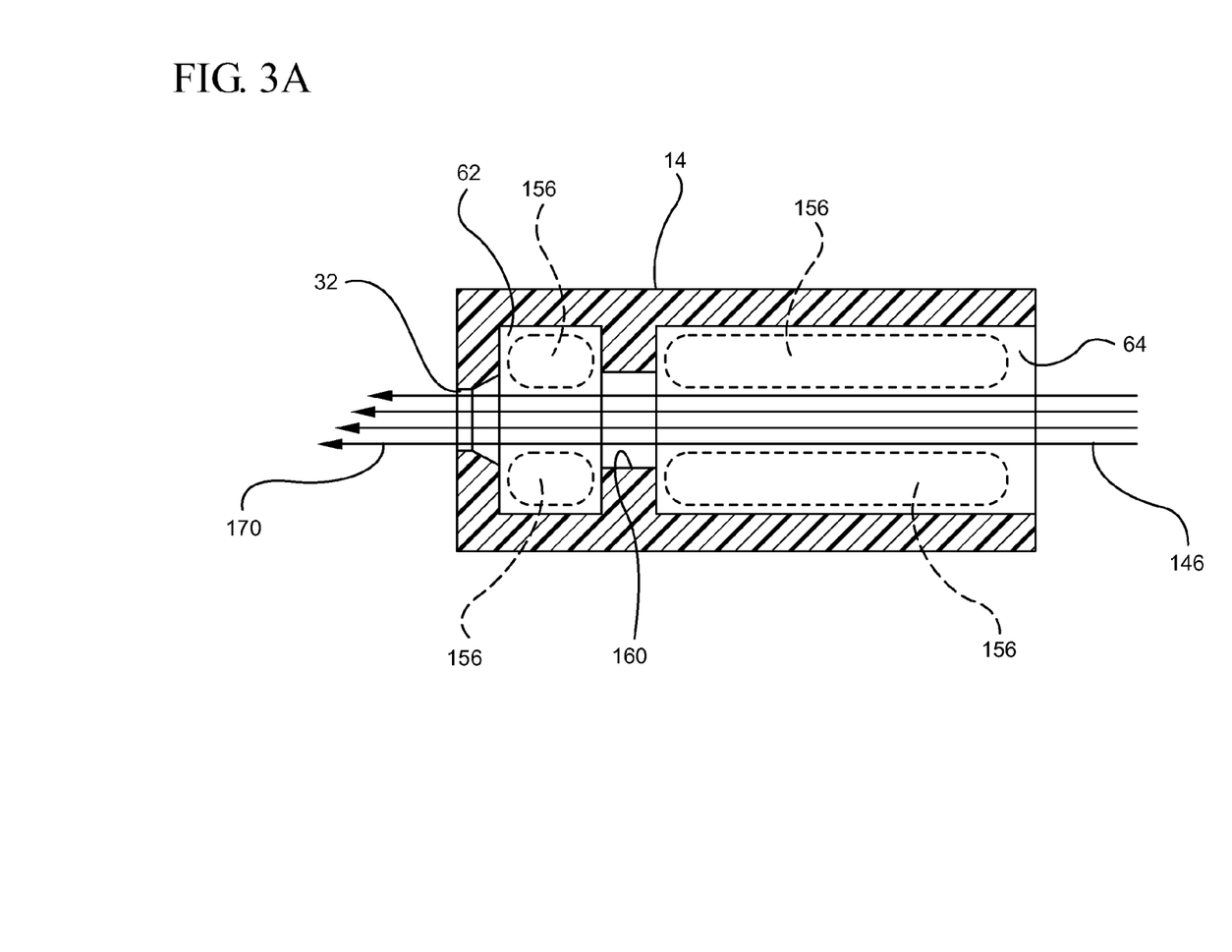
FIG. 3A is a cross-sectioned view of an interior lumen of a catheter adapter demonstrating fluid flow without the presence of a septum activator in accordance with a representative embodiment of the present invention.

Referring now to FIG. 3A, a cross-section view of an interior lumen of a catheter adapter 14 is shown. In some embodiments, catheter adapter 14 includes a forward fluid chamber 62 and a rearward fluid chamber 64 fluidly connected via a narrowed channel or port 160. As configured and in some embodiments, a fluid pathway 170 is defined whereby a fluid 146 flows downstream from the rearward fluid chamber 64, through the port 160 and into the forward fluid chamber 62. The fluid pathway 170 continues through the forward fluid chamber 62 and exits the distal end 32 into a catheter (not shown) or other downstream conduit. While fluid 146 fills the entire lumen of the catheter adapter 14, the fluid pathway 170 is generally restricted to a narrow pathway through a central portion of the cross-section of the catheter adapter 14. Accordingly, fluid 146 that is not part of the narrow fluid pathway 170 stagnates or circulates within dead zones 156. Fluid 146 trapped within these dead zones is prevented from sufficiently mixing with fluid 146 in the fluid pathway 170. In some embodiments, stagnation results in increased, localized concentrations of chemicals, bodily fluids and/or medicaments that may lead to precipitation, coagulation or administration of dangerously high doses of medications. Therefore, in some embodiments of the present invention, a septum activator 80 is provided having features to eliminate dead zones 156 within the catheter adapter 14 lumen.

Figure 3B:
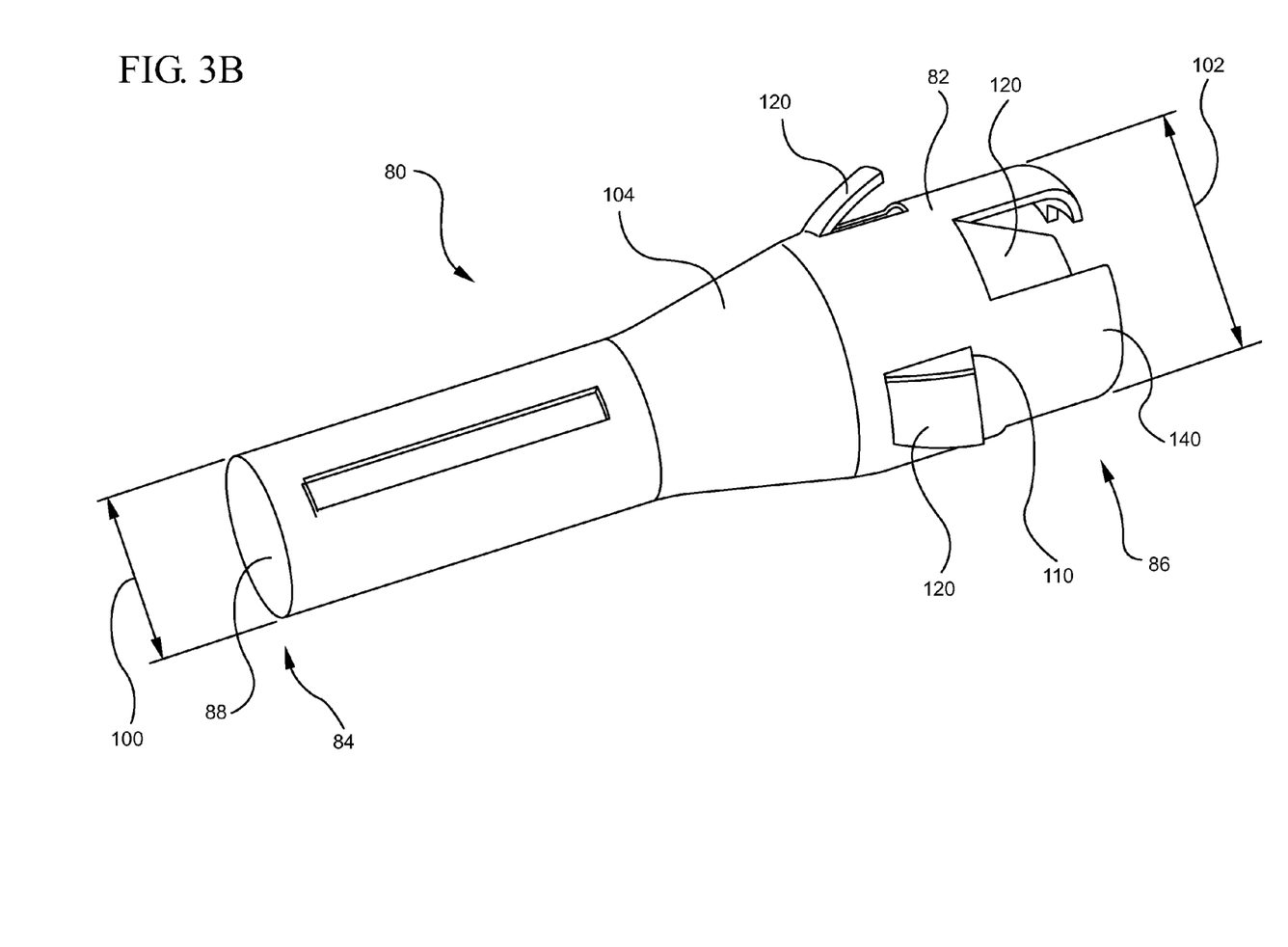
FIG. 3B is a perspective view of an embodiment of a septum activator in accordance with the present invention.

Referring now to FIG. 3B, a perspective view of the septum activator 80 is shown. In some embodiments, the distal end 84 of the tubular body 82 comprises a first diameter 100 that is less than a second diameter 102 of the proximal end 86. The narrower distal end 84 is configured to compatibly insert within the opening 54 of the septum 50, while the wider proximal end 86 is configured to compatibly seat within the rearward chamber 64 of the catheter adapter 14. In some embodiments, the septum activator further includes a tapered middle section 104 to couple the distal 84 and proximal 86 ends.

Figure 5:
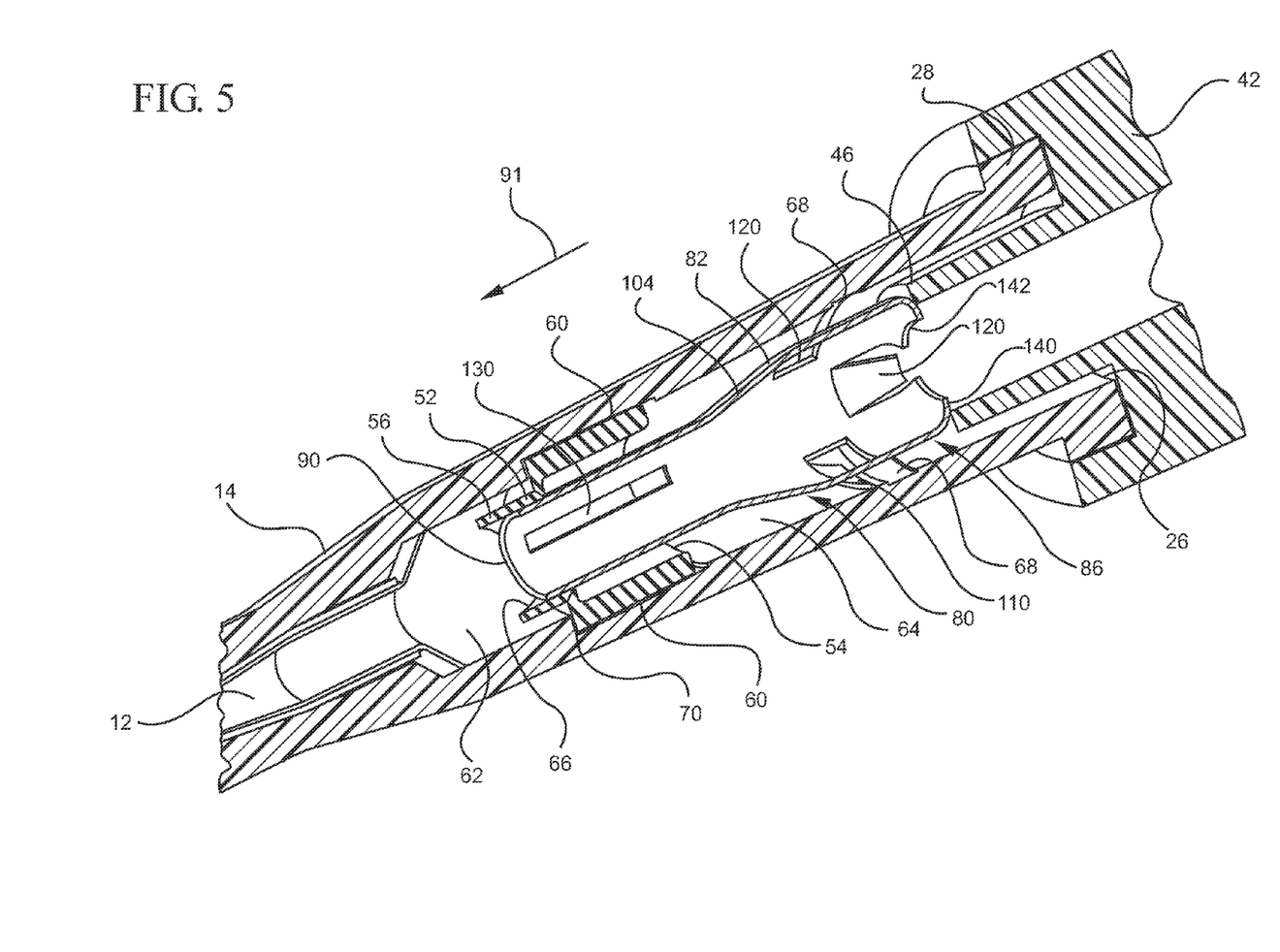
FIG. 5 is a cross-sectioned view of an assembled catheter assembly in accordance with the present invention, following activation.

In some embodiments, the proximal end 86 of the septum activator 80 further includes a retention spring 110. The retention spring 110 generally comprises an outwardly biased portion of the tubular body 82 configured to compatibly engage a septum activator retention groove 68, as shown in FIGS. 2A, and 4-5. The interaction between the retention spring 110 and the groove 68 limits the lateral movement of the septum activator 80 within the lumen 16 of the catheter adapter 14. Thus, the width of the retention groove 68 determines or limits the distance of travel for the septum activator 80 within the catheter adapter 14. Additionally, the interaction between retention spring 110 and the groove 68 prevents removal of the septum activator 80 from the catheter adapter 14. In some embodiments, the septum activator 80 comprises a plurality of retention springs 110, while in other embodiments the septum activator 80 comprises a single retention spring 110.

In some embodiments, the septum activator 80 further comprises features for directing or diverting fluid flow around and/or through the septum activator 80. Flow diversion may be important to prevent the stagnation or coagulation of fluids within dead zones 156 of the septum activator 80 and/or the lumen 16 of the catheter adapter 14 resulting in blockages. Additionally, stagnation of fluid flow through the catheter assembly 10 may result in a build up of undesirable concentrations of medicaments within the catheter adapter 14 and/or the septum activator 80, as previously discussed. Undesirable high concentrations may result in ineffective treatment causing serious side effects, including death. Thus, in some embodiments the septum activator 80 is modified to include flow deflectors 120 and flow diversion channels 130 to provide a flushable catheter assembly 10 system.

The flow deflectors 120 generally comprise inwardly and outwardly angled portions of the septum activator 80 outer surface. The flow deflectors 120 are positioned so as to be protrude into a flow path through the catheter adapter 14. Thus, as the fluid contacts the flow deflectors 120 the path of the fluid flow is disturbed. This disturbance results in redirecting the fluid flow both through the inner lumen 88 of the septum activator 80, and between the outer surface of the septum activator 80 and the inner surface 24 of the catheter adapter 14. In some embodiment, the retention spring 110 also serves as a flow deflector 120.

A flow diversion channel 130 is provided to permit exchange of fluid between the lumen of the catheter adapter 16 and the inner lumen 88 of the septum activator 80. Thus, the flow diversion channel 130 prevents stagnation and/or clotting of fluid between the inner surface 24 of the catheter adapter 14 and the outer surface of the septum activator 80. In some embodiments, the flow diversion channel 130 comprises a window or opening in the surface of the tubular body 82. In other embodiments, the flow diversion channel 130 further comprises a flap or angled surface to further direct fluid to flow through the channel 130.

The proximal end 86 of the septum activator 80 further includes a contact surface 140. The contact surface 140 comprises the most proximal end portion of the septum activator 80 and is positioned within the rearward chamber 64 of the catheter adapter 14 adjacent to the proximal opening 26 of the catheter adapter 14, as shown in FIG. 4, below.

Figure 3C:
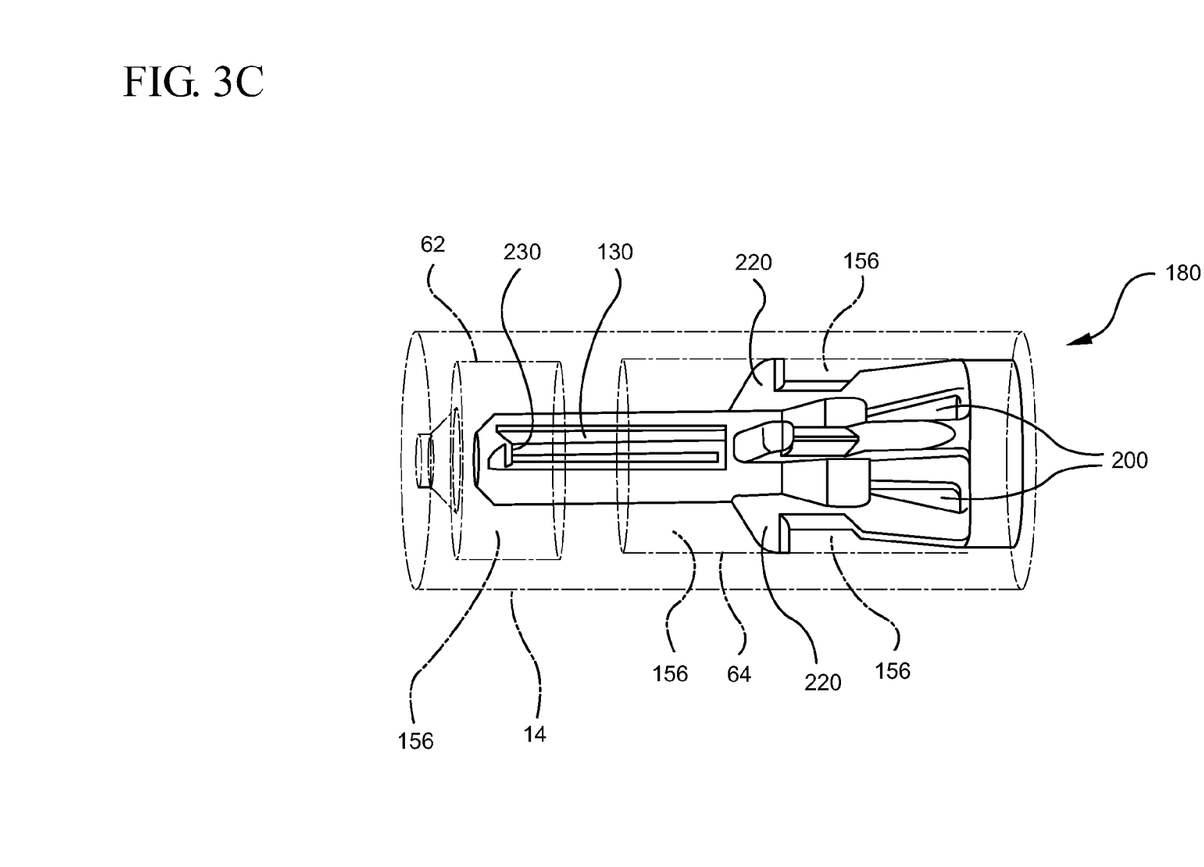
FIG. 3C is a side view of an embodiment of a septum activator disposed in an inner lumen of a catheter adapter in accordance with the present invention, following activation.

Referring now to FIG. 3C, an embodiment of a septum activator 180 is shown as positioned in the lumen of a catheter adapter 14 (shown in phantom). In some embodiments, septum activator 180 is configured to include various re-circulation features. For example, in some embodiments septum activator 180 includes various vents 200 configured to divert fluid from the fluid pathway 170 into the dead zones 156. Thus, as fluid flows into and through the septum activator 180, the fluid within the septum activator 180 passes through the vents 200 and into the dead zones 156 between the outer surface of the activator 180 and the inner wall surface of the catheter adapter 14. The diverted fluid intermixes with the fluid in the dead zones 156 to flush fluid from the dead zones 156 and prevent stagnation and/or overconcentration, as previously discussed.

In some embodiments, septum activator 180 is further modified to include flushing fins 220. Flushing fins 220 generally comprise perpendicular extension of the outer surface of the activator 180 that extend into the dead zones 156 between the activator 180 and the inner wall surface of the catheter adapter 14. The flushing fins 220 are provided to divert and redirect fluid within the fluid pathway 170 into the dead zones 156. As such, fluid within the dead zones 156 is intermixed with fluid in the fluid pathway 170 to prevent stagnation and/or overconcentration of fluid within the catheter adapter 14.

Finally, in some embodiments the flow diversion channel 130 is modified to include a flow deflector 230. The flow deflector 230 comprises a beveled, distal surface of the deflector 230 positioned to divert fluid within the fluid pathway 170 into the dead zones 156 of the forward fluid chamber 62. Thus, as fluid 146 flows through the septum activator 180, a portion of the fluid is diverted through the flow diversion channel 130 and into the dead zone 156 via the flow deflector 230, as shown in FIG. 3D.

Figure 3D:
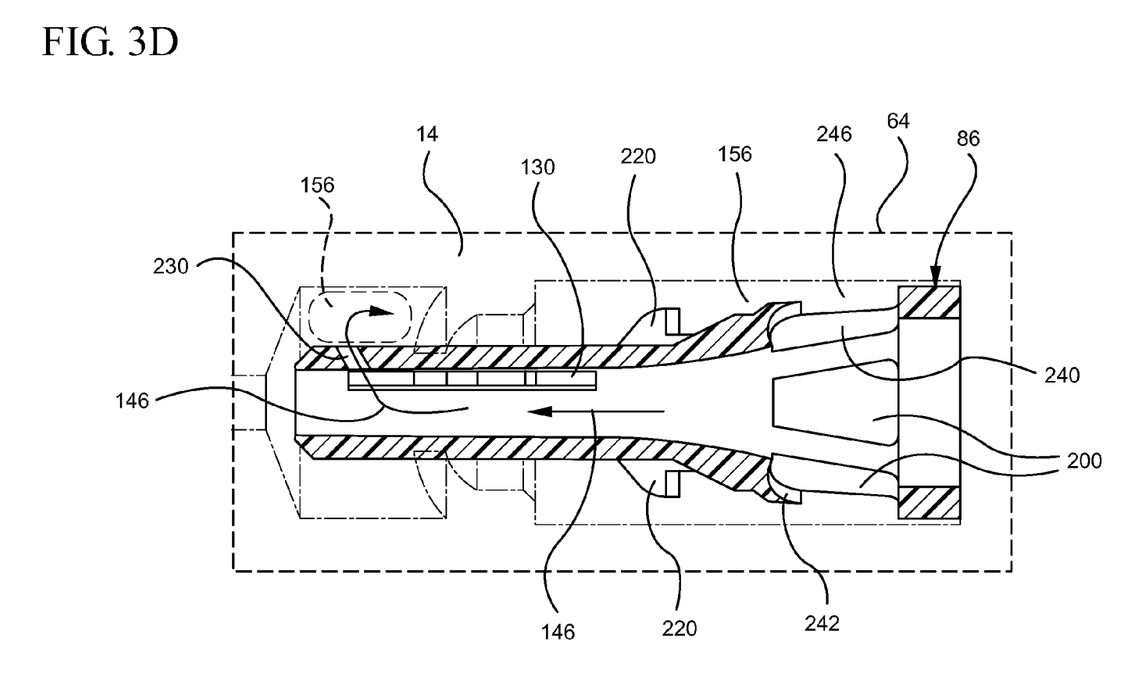
FIG. 3D is a side view of an embodiment of a septum activator disposed in an inner lumen of a catheter adapter in accordance with the present invention, demonstrating fluid flow through the catheter adapter.

With continued reference to FIG. 3D, a cross-sectioned septum activator 180 positioned within a cross-sectioned catheter adapter 14. As previously discussed, recirculation features may be added to both the proximal 86 and distal 186 ends of the septum activator 180. In some embodiments, the proximal end 86 of the septum activator 180 is modified to include curved window features 240 that redirect the flow of a fluid 246 into the dead zones 156 of the rearward fluid chamber 64. Thus, the curved surface 242 of the window feature 240 alone and/or in combination with the other recirculation features promotes intermixing of the fluid within the dead zones 156 to prevent stagnation and overconcentration of fluids within the catheter adapter 14.

In some embodiments, the recirculation features are positioned in a symmetrical configuration to induce best flushing. In other embodiments, the recirculation features are positioned in an asymmetrical configuration to induce best flushing. Finally, in some embodiments the recirculation features are used in combination with additional diffusing, circulating and recirculating features of the septum activator 180 to aid the fluid flushing capability of the septum activator 180. A person having ordinary skill in the art will appreciate that in light of the foregoing disclosure, additional surfaces of the septum activator 180 may be modified to increase or decrease flow efficiency, mixing and flushing of fluids within the septum activator 180, as desired.

Referring now to FIG. 4, a cross-sectional view of the assembled catheter assembly 10 is shown prior to activation of the septum 50 via the septum activator 80. Prior to activation, the septum activator 80 is entirely positioned within the rearward fluid chamber 64 of the catheter adapter 14. Additionally, the retention springs 110 are engaged within the retention groove 68 and positioned near the proximal end of the retention groove 68. The contact surface 140 of the septum activator 80 is positioned near the opening 26 of the catheter adapter 14, such that a proximal opening 142 of the septum activator 80 is in a plane generally parallel to the plane of the catheter adapter opening 26. Finally, the outwardly biased retention springs 110 bind on the surface of the groove 68 thereby maintaining the inactivated position of the septum activator 80 within the catheter adapter 14.

Referring now to FIG. 5, a cross-sectional view of the catheter assembly 10 is shown following activation of the septum 50 via the septum activator 80. Upon insertion of the coupler 42 into the proximal opening 26 of the catheter adapter 14, the probe portion 46 of the coupler 42 contacts the contact surface 140 of the septum activator 80. The septum activator 80 is advanced in a distal direction 91 as the coupler 42 is further inserted into the proximal opening 26 of the catheter adapter 14. As the coupler 42 is advanced further into the proximal opening 26, the probing surface 90 of the septum activator 80 passes through the barrier surface 52 of septum 50. As such, the probing surface 90 of the septum activator 80 is positioned within the forward chamber 62 providing a fluid pathway through the septum 50.

In some embodiments, the catheter assembly 10 is configured to permit the septum activator 80 to return to a position entirely within the rearward chamber 64 following removal of the coupler 42 from the catheter adapter 14. Thus, when the coupler 46 is removed or detached from the catheter assembly 10, the fluid pathway through the septum 50 is reclosed. In some embodiments, the retention spring 110 is configured to flex inwardly upon contact between the contact surface 140 of the septum activator 80 and the probe 46 of the coupler 42. When the retention spring 110 flexes inwardly, the probing surface 90 of the septum activator 80 is temporarily advanced in a distal direction 91 to bias open the slits 66 and 56, or the leak orifice 58. When contact between the probe 46 and the contact surface 140 ceases, the retention spring 110 returns to its relaxed position. The relaxed position withdrawals the probing surface 90 of the septum activator 80 from the barrier surface 52 thereby permitting closure of the slits 66 and 56.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A flushable catheter assembly, comprising:
   a catheter adapter having a distal end, a proximal end, an inner surface, an outer surface, and an inner lumen;
   a flow path extending through the inner lumen of the catheter adapter;
   a groove formed on the inner surface and located within the inner lumen;
   a septum entirely disposed within the groove, the septum having an outer surface and a length, the length of the septum being approximately equal to a length of the groove;
   a ventilation channel formed in the groove, such that an air flow is interposed between the outer surface of the septum and the ventilation channel along the entire length of the septum;
   a coating applied to a surface of the ventilation channel; and
   a septum activator entirely disposed within the inner lumen of the catheter adapter, the septum activator having a distal end, a proximal end and a fluid channel, wherein the distal end of the septum activator is positioned adjacent to the septum and the proximal end of the septum activator is positioned adjacent to the proximal end of the catheter adapter, the distal end of the septum activator being configured to bias the septum into an opened position.

2. The catheter assembly of claim 1, wherein the septum activator further comprises a retention tab, and the inner surface of the catheter adapter further comprises a retention groove for receiving the retention tab.

3. The catheter assembly of claim 1, wherein the septum activator further comprises:
   a flow deflector that extends outwardly from an outward surface of the septum activator and into the flow path;
   an elongate channel providing fluid communication between an inner lumen of the septum activator and the flow path; and
   one or more vents positioned on the proximal end of the septum activator, the one or more vents providing fluid communication between the inner lumen of the septum activator and the flow path.

4. The catheter assembly of claim 1, wherein the coating comprises at least one of a hydrophobic material and a swelling polymer material.

5. The catheter assembly of claim 1, further comprising a luer adapter forming a portion of the outer surface of the proximal end of the catheter adapter.

6. The catheter assembly of claim 1, wherein the proximal end of the septum activator further comprises a contact surface for forming an interface with a probe, wherein the probe is inserted into the proximal end of the catheter adapter and contacts the contact surface of the septum activator to bias the septum activator in the distal direction.

7. A method for manufacturing a flushable catheter assembly, the method comprising:
   providing a catheter adapter having a distal end, a proximal end, an inner surface, an outer surface, and a flow path extending through an inner lumen of the catheter adapter;
   forming a groove on the inner surface of the catheter adapter;

providing a septum having an outer surface and a length, a length of the septum being approximately equal to a length of the groove;

disposing the entire length of the septum within the groove to secure the septum within the groove;

providing a plurality of ventilation channels within the groove, such that an air flow is interposed between the outer surface of the septum and the plurality of ventilation channels along the entire length of the septum;

applying a hydrophobic coating to a surface of the plurality of ventilation channels; and disposing a septum activator entirely within the inner lumen of the catheter adapter thereby securing the septum within the groove, the septum activator having a distal end, a proximal end and a fluid channel, the distal end of the septum activator being positioned adjacent to the septum and the proximal end of the septum activator being positioned adjacent to the proximal end of the catheter adapter, wherein the distal end of the septum activator biases the septum to an opened position upon translating the septum activator through the inner lumen of the catheter adapter in a distal direction.

8. The method of claim 7, further comprising the steps of providing a retention tab to an external surface of the septum activator, and providing a retention groove on the inner surface of the catheter adapter, wherein the retention groove receives the retention tab to substantially retain the septum activator within the inner lumen of the catheter adapter.

9. The method of claim 7, further comprising providing a flow diversion channel on a surface of the septum activator, the flow diversion channel comprising an elongate channel providing fluid communication between an inner lumen of the septum activator and the flow path.

10. The method of claim 7, further comprising providing a flow deflector on a surface of the septum activator, the flow deflector extending outwardly from an outer surface of the septum activator and into the flow path.

11. The method of claim 7, further comprising providing a luer adapter on a proximal end of the outer surface of the catheter adapter.

12. The method of claim 7, further comprising providing a contact surface on the proximal end of the septum activator for forming an interface with a probe, wherein the probe is inserted into the proximal end of the catheter adapter and contacts the contact surface of the septum activator to bias the septum activator in the distal direction.

* * * * *